(12) United States Patent
Kunzmann

(10) Patent No.: US 8,121,247 B2
(45) Date of Patent: Feb. 21, 2012

(54) METHOD FOR THE TOMOGRAPHIC MEASUREMENT OF MECHANICAL WORKPIECES

(75) Inventor: Steffen Kunzmann, Dresden (DE)

(73) Assignee: Carl Zeiss Industrielle Messtechnik GmbH, Oberkochen (DE)

( * ) Notice: Subject to any disclaimer, the term of this patent is extended or adjusted under 35 U.S.C. 154(b) by 0 days.

(21) Appl. No.: 12/898,913

(22) Filed: Oct. 6, 2010

(65) Prior Publication Data

US 2011/0096896 A1  Apr. 28, 2011

Related U.S. Application Data

(63) Continuation of application No. PCT/EP2009/002331, filed on Mar. 31, 2009.

(30) Foreign Application Priority Data

Apr. 7, 2008 (DE) .......................... 10 2008 018 445

(51) Int. Cl.
  *A61B 6/00* (2006.01)
(52) U.S. Cl. ............... 378/4; 382/131; 382/132; 378/19
(58) Field of Classification Search ........................ 378/4
  See application file for complete search history.

(56) References Cited

U.S. PATENT DOCUMENTS

| | | | |
|---|---|---|---|
| 5,124,914 A | | 6/1992 | Grangeat |
| 5,559,334 A | | 9/1996 | Gupta et al. |
| 5,951,475 A | * | 9/1999 | Gueziec et al. ............... 600/425 |
| 6,028,912 A | | 2/2000 | Navab |
| 6,112,109 A | * | 8/2000 | D'Urso .......................... 600/407 |
| 6,341,153 B1 | | 1/2002 | Rivera et al. |
| 6,591,004 B1 | * | 7/2003 | VanEssen et al. ............. 382/154 |
| 7,099,435 B2 | | 8/2006 | Heumann et al. |
| 7,203,267 B2 | | 4/2007 | De Man et al. |
| 7,264,397 B2 | * | 9/2007 | Ritter ............................. 378/205 |
| 7,477,776 B2 | * | 1/2009 | Lachner et al. ................ 382/154 |
| 7,487,063 B2 | * | 2/2009 | Tubic et al. .................... 702/152 |

(Continued)

FOREIGN PATENT DOCUMENTS

DE  10 2005 028 420 A1  12/2006

(Continued)

OTHER PUBLICATIONS

Nikkhahe-Dehkordi et al., 3D reconstruction of the femoral bone using two x-ray images from orthogonal views, computer assisted radiology, CAR '96, Spring-Verlag, 1996, pp. 6.*

(Continued)

*Primary Examiner* — Alexander H Taningco
(74) *Attorney, Agent, or Firm* — Harness, Dickey & Pierce, P.L.C.

(57) ABSTRACT

In a method for measuring mechanical workpieces by tomography, a workpiece and radiation penetrating the workpiece are moved relative to one another step-by-step. A two-dimensional image of the workpiece is generated in an imaging plane from the interaction of the workpiece and the radiation in each movement position of the workpiece. In addition, a three-dimensional representation of the workpiece is computed from the two-dimensional images. From at least two two-dimensional images showing a regular actual structure existing within the workpiece, points at a high-contrast transition are registered. A three-dimensional equivalent body is determined from the position of the points, and said equivalent body is compared to a predefined nominal structure.

16 Claims, 5 Drawing Sheets

U.S. PATENT DOCUMENTS

| | | | |
|---|---|---|---|
| 7,657,075 B2 * | 2/2010 | Viswanathan | 382/132 |
| 2003/0099323 A1 * | 5/2003 | Nagata et al. | 378/4 |
| 2006/0262970 A1 * | 11/2006 | Boese et al. | 382/131 |
| 2008/0089589 A1 | 4/2008 | Lettenbauer et al. | |
| 2008/0217559 A1 | 9/2008 | Poglitsch et al. | |

FOREIGN PATENT DOCUMENTS

| | | |
|---|---|---|
| DE | 10 2005 032 686 A1 | 1/2007 |
| DE | 10 2005 032 687 A1 | 1/2007 |
| DE | 10 2005 033 187 A1 | 1/2007 |
| GB | 2 222 356 A | 2/1990 |

OTHER PUBLICATIONS

Szymezak et al., 3d shape from silhouette points in registered 2d images using conjugate gradient method, Medical Imaging, Image processing Proc, SPIE, 7623, 2010, pp. 8.*

Kurazume et al., 3d reconstruction of a femoral shape using a parametric model and two 2d fluoroscopic images, Computer Vision and Image Understanding, 2008, pp. 202-211.*

* cited by examiner

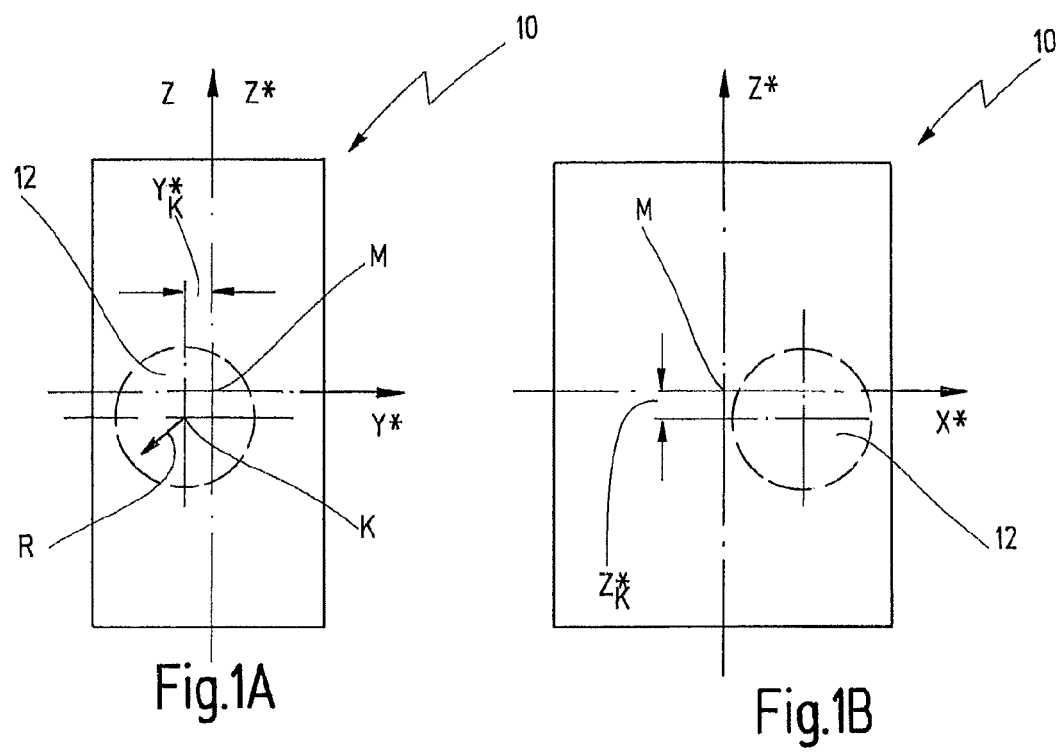
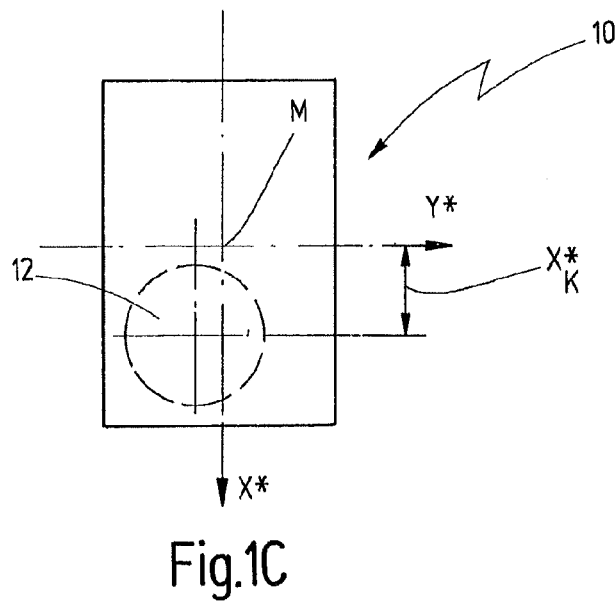
Fig.1A  Fig.1B  Fig.1C

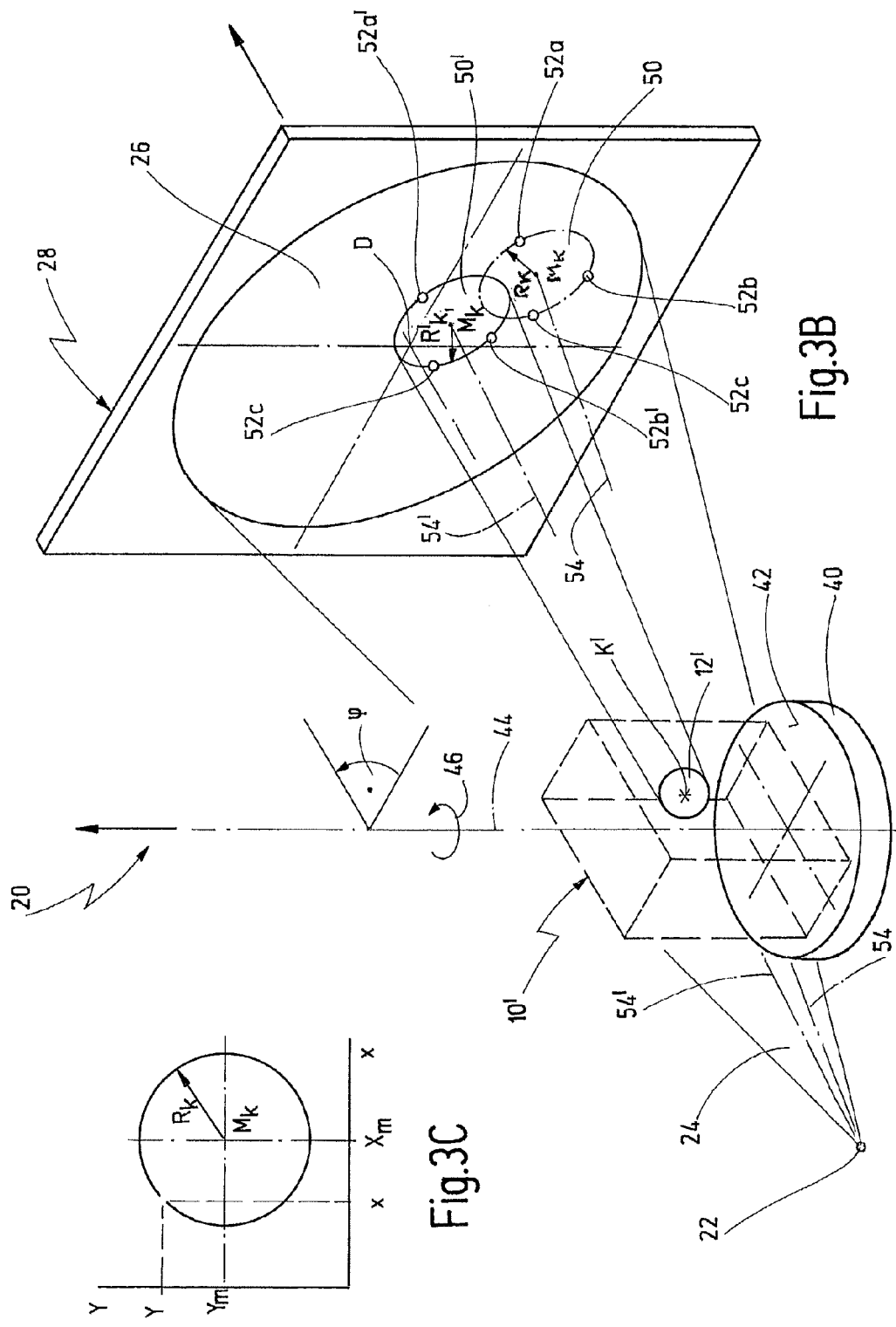

US 8,121,247 B2

METHOD FOR THE TOMOGRAPHIC MEASUREMENT OF MECHANICAL WORKPIECES

CROSS REFERENCES TO RELATED APPLICATIONS

This application is a continuation of international patent application PCT/EP2009/002331 filed on Mar. 31, 2009 designating the U.S., which international patent application has been published in German language and claims priority from German patent application DE 10 2008 018 445.4 filed on Apr. 7, 2008. The entire contents of these priority applications are incorporated herein by reference.

BACKGROUND OF THE INVENTION

The invention relates to a method for measuring mechanical workpieces by tomography.

In the production of, in particular, high-quality mechanical workpieces, it is necessary for the workpiece to be measured after or even during the production and processing in order to check if certain measurement points on the workpiece defined in advance meet predefined dimensions within some tolerances likewise defined in advance. For this purpose, use is often made of multi-coordinate measurement machines, which scan the workpiece by means of touch probes and monitor the dimensional accuracy of the workpiece surfaces in this fashion.

As an alternative, a different measurement approach has been used for some time now for measuring mechanical workpieces, which approach was initially used in medicine as an imaging method for examining human bodies, namely the method of computer tomography (CT). In medical applications, the body or body region to be examined is irradiated in a plane by means of a linear array of X-ray radiation sources. On the opposite side of the body, a corresponding array of X-ray detectors is situated opposite the array of X-ray radiation sources. This pair of arrays is then rotated by an angular step about an axis running perpendicular to the plane, and a further recording is produced. After the array has been rotated, step-by-step, through a total of 360°, a cross-sectional image in the plane is computed from the individual recordings, which image reproduces the density distribution in this plane. If the body and the pair of arrays are now subsequently displaced relative to one another by a linear step along the axis, a further, immediately adjacent cross-sectional image can be generated and a three-dimensional display of the body or body region can be generated from a plurality of such adjacent cross-sectional images. This measurement method is rather complicated because a human body has a very complex density distribution with density varying in large regions, and the structures to be recorded can differ significantly and can be of unforeseeable type and shape.

By contrast, workpieces in quality control are often objects with only two densities, namely the density of the material of the workpiece and the density of air. Furthermore, the structures to be examined during quality control are known and merely have to be examined with respect to deviations.

DE 10 2005 039 422 A1 describes a computer tomography method, simplified with respect to medical applications, for examining workpieces. In this method, a mechanical workpiece is situated on a rotary table between a spot-like X-ray radiation source and an areal detector array. Here, the rotational axis of the rotary table runs substantially perpendicular to the radiation direction. The workpiece is penetrated by the X-ray radiation, and a shadow image of the workpiece is created on the detector array. The workpiece is then successively rotated by an angular step, for example 800 or 1200 times, on the rotary table and additional shadow images are created. A three-dimensional image of the workpiece is then computed from the plurality of shadow images, for example according to a method of back-projection, as described in DE 39 24 066 A1.

Computer tomography measuring stations of this type are commercially offered, for example by the assignee of the invention under the brand name "Metrotom" (www.zeiss.de/imt).

With prior art measuring stations, a so-called "reconstruction" is performed, i.e. a complete three-dimensional image of the density distribution of the measurement object (mechanical workpiece) is computed with a predefined resolution of volume elements (voxels). In order to be able to do this with sufficiently high precision for workpiece measuring, a large number of individual images are required, in practice between 360 and 1080, corresponding to angular steps of the rotary table between 1° and ⅓°. However, a certain amount of time is required for each rotational step in order to accelerate the rotary table from its rest position, to move it, and to decelerate it again until it rests. Furthermore, a certain amount of time is required to calculate the three-dimensional image, even though this can already be started during the measurement acquisition, and so, overall, prior art measuring stations require between 15 and 30 minutes for a complete measurement. In many cases, this measuring time is unacceptable.

SUMMARY OF THE INVENTION

The invention therefore has the object of providing a method for measuring a mechanical workpiece by tomography, but avoids the aforementioned disadvantages. More particularly, a method is to be provided that requires a significantly shorter overall measurement time.

According to an aspect of the invention, there is provided a method for measuring mechanical workpieces having a defined rotationally symmetric structure, the method comprising the steps of providing a radiation source for generating radiation, providing a detector array for receiving the radiation, said detector array defining a two-dimensional imaging plane, positioning a workpiece between the radiation source and the detector array, so that the radiation penetrates the workpiece before it impinges on the detector array, moving the radiation source and the workpiece relative to one another in a step-by-step fashion, generating a number of two-dimensional images of the workpiece by means of the detector array for a plurality of movement positions of the workpiece, and computing a three-dimensional image of the structure from the two-dimensional images, wherein the step of computing comprises detecting a high-contrast transition, which may correspond to edges of the structure, in said two-dimensional images, registering points at said high-contrast transition from at least two two-dimensional images generated at two different movement positions, and determining a three-dimensional geometric equivalent body using the registered points, and comparing said equivalent body to a predefined nominal structure, wherein the geometric equivalent body only parameterizes said rotationally symmetric structure.

According to another aspect, there is provided a method for measuring mechanical workpieces having a rotationally symmetric structure, wherein a workpiece and radiation from a radiation source penetrating the workpiece are moved relative to one another step-by-step, wherein a two-dimensional image of the workpiece is generated in an imaging plane from the interaction of the workpiece and the radiation in each movement position of the workpiece, and wherein a three-dimensional image of the structure is computed from the two-dimensional images, wherein, from at least two two-dimensional images of the workpiece generated at two different movement positions, points which may correspond to edges of the structure are registered at a high-contrast transition in said two-dimensional images, wherein a three-dimensional geometric equivalent body is determined from the position of the registered points, wherein said equivalent body is compared to a predefined nominal structure, and wherein the geometric equivalent body only parameterizes individual rotationally symmetric elements of the workpiece, which are imaged in the two-dimensional images with clear-cut, high-contrast object boundaries.

It has turned out that, in contrast to natural objects in medicine, the regularity of the shape of certain structures in mechanical workpieces (bores, grooves, etc.) can be advantageously used to drastically reduce the overall measuring time by generating an equivalent body of this structure from relatively few measurement points, thereby exploiting the known regularity of the structure. Only a few, preferably rotationally symmetric, elements are measured by tomography in a calibrated recording device with a two-dimensional projection from a plurality of directions, and these are parameterized by geometric equivalent bodies. This procedure differs from conventional methods in the prior art, because the entire density distribution must be reconstructed in a voxel matrix in those cases.

Use is made of the fact that a large number of the elements to be examined in the reconstruction volume are regular, and in particular rotationally symmetric, and these elements typically image with clear-cut, high-contrast object boundaries in the individual projections. These object boundaries can be extracted from the individual projections with the aid of image-processing methods, for example with a suitable edge recognition. Once a plurality of projections have been recorded at different, known orientations, the position, the axial direction and further shape parameters, such as a radius or a cone angle, of the three-dimensional element can be determined therefrom.

The new method may dispense with conventional complete recording of all projection images of a CT scan. In principle, two projections alone can be used to approximately determine the parameters of the three-dimensional structure to be examined.

As a consequence, computational-time expensive CT reconstruction of an entire voxel matrix required until now may be dispensed with. First tests have resulted in this reducing the overall measuring time from the conventional 15 to 30 minutes to less than 1 minute.

In preferred embodiments, the regular nominal structure is a rotationally symmetric structure, and in particular a sphere, a cylinder or a cone.

In a preferred refinement of the method according to the invention, the radiation source and the imaging plane for the relative movement are fixed in space and the workpiece is rotated about a rotational axis in predefined angular steps.

The advantage of this measure lies in the fact that use can be made of established components in respect of the measuring station.

In a further exemplary embodiment, the coordinates of a center and a radius of the equivalent body are determined in the case of a spherical nominal structure.

The advantage of this measure lies in the fact that a rough approximation of the equivalent body is possible with a minimum number of parameters and hence with a minimum amount of effort.

In the case of both of the aforementioned exemplary embodiments, a particularly preferred refinement is comprises that the following steps are used to determine the position of the center of the equivalent body:

a) determining the coordinates of at least three points on the boundary of the circular, two-dimensional image of the actual structure in a first movement position of the workpiece;

b) determining a first center point of the circular image from the coordinates of the three points;

c) rotating the workpiece on the one hand and, on the other hand, the radiation source and imaging plane relative to one another by a predefined angular step from the first into a second movement position of the workpiece;

d) determining the coordinates of at least three points on the boundary of the moved circular, two-dimensional image of the actual structure in the second movement position of the workpiece;

e) determining a second center point of the moved circular image from the coordinates of the three points;

f) determining two center beams between the radiation source and the first and second center points;

g) determining the position of the smallest distance between the center beams;

h) dropping the connection perpendicular between the center beams at the position of the smallest distance; and i) determining the coordinates of the center point of the connection perpendicular as the position of the center of the equivalent body.

In addition, it is particularly preferable if the following steps are followed to determine the radius ($R_A$) of the equivalent body:

j) determining a first distance between the radiation source and the center point of the circular image;

k) determining a second distance between the radiation source and the center point of the actual structure; and l) multiplying the radius of the circular image by the ratio between the second and the first distance.

The advantage of these measures lie in the fact that the mentioned few parameters of the spherical structure can be determined using few operations.

In a refinement of the aforementioned exemplary embodiment, tangent points are determined for a plurality of the points established in step a), at which tangent points a connection beam between the radiation source and the points touches a boundary of the actual structure generating the image, and the equivalent body is fitted into the point cloud formed by the points using the values established in steps i) and l) for the position of the center point and the radius of the equivalent body as initial values.

The advantage of this measure lies in the fact that the accuracy of the fit can be significantly improved.

This holds true even more if the point cloud is formed from tangent points established in different rotational positions of the workpiece.

Further advantages emerge from the description and the attached drawing. It is understood that the aforementioned features and the features yet to be explained below can be used not only in the respectively specified combination, but also in other combinations or on their own, without departing from the scope of the present invention.

BRIEF DESCRIPTION OF THE DRAWINGS

Exemplary embodiments of the invention are illustrated in the drawing and are explained in more detail in the following description, in which:

FIGS. 1A-C show a technical drawing, in three orthogonal views, of a mechanical workpiece as can be measured by the method according to the invention;

FIGS. 3A-B show a perspective view of the measuring station from FIGS. 2A-B in a first rotational position of the workpiece and in a second rotational position of the workpiece;

FIG. 3C shows an illustration to explain an equation of a circle;

DESCRIPTION OF PREFERRED EMBODIMENTS

Figure 2A:
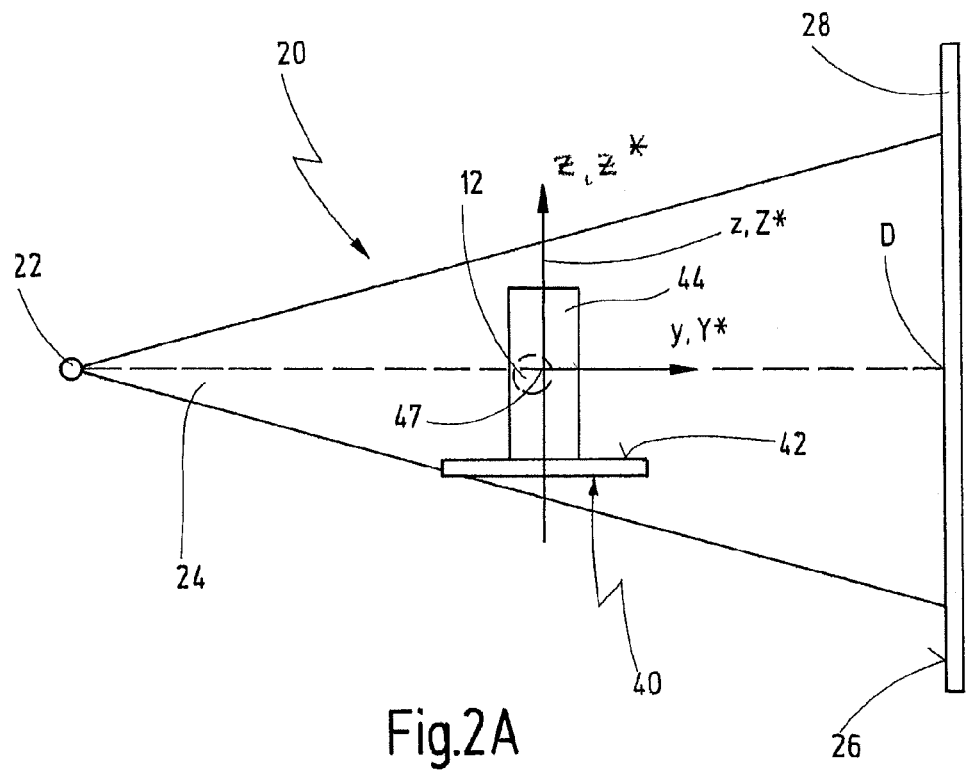
FIGS. 2A-B show an extremely schematic view, in a side view and plan view, respectively, of a measuring station for carrying out the method according to the invention.

FIGS. 1A-1C illustrate three mutually perpendicular views of a workpiece denoted by reference numeral 10. In the illustrated simplified example, workpiece 10 is a cuboid body. The workpiece 10 consists of a known material, assumed to be homogeneous, i.e. having no variations of density therein.

In the illustrated exemplary embodiment, the workpiece 10 has a spherical inner structure 12, the center point of which is denoted by K and the radius of which is denoted by R. Compared to the rest of the workpiece 10, the structure 12 has different properties, more particularly a different density. In the illustrated example, said structure can be a spherical, air-filled cavity in the workpiece 10.

The structure 12 is an actual structure produced within the workpiece 10 in some production process. Therefore, structure 12 in practice does not correspond exactly to a nominal structure predefined by the designer in either position or shape, which nominal structure for example is saved in a CAD file. It is the object of the present method to determine to what extent the actual structure 12 deviates from the desired contour. For this purpose, the actual structure 12 is measured and approximated to the best possible extent by an optimally fitted equivalent body. The characteristic data of the equivalent body, i.e. the location of the center point K in the workpiece 10 and the radius R in the illustrated exemplary embodiment, are then compared to the constructional predefined data of the nominal structure. Whether the workpiece 10 lies within predefined tolerances in respect of the structure is derived from this comparison.

It goes without saying that the workpiece and the inner structure can also have a different shape. The workpiece is preferably a component of a machine or an instrument of arbitrary shape, in and/or on which there are structures of basically regular geometric shape, for example of cylindrical, conical, parabolic, spiral or any other regular shape. Here, the term "regular" should be understood to mean that the shape can be determined mathematically in a manner that is acceptable for the present application in respect of the computational-time expenditure.

FIGS. 2A-B and 3A-B illustrate how the workpiece 10 is measured by tomography.

To this end, the workpiece 10 is arranged in a measuring station 20. The measuring station 20 comprises a spot-like radiation source 22, which is preferably embodied as an X-ray source and irradiates the workpiece 10 from the side. The radiation source 22 is arranged fixed in space and emits a conical radiation 24. The radiation 24 penetrates the workpiece 10 and is incident on a circular region 26 of a detector array 28 arranged behind the workpiece 10.

Here it is understood that the spot-like X-ray radiation source 22 should only be understood to be exemplary. It goes without saying that other radiation sources, for example linear arrays of radiation sources, can also be used within the scope of the present invention. Furthermore, it is also possible to use other imaging examination methods, such as NMR tomography.

The detector array 28 is planar and rectangular, preferably square, and has edges $29a$-$29d$. On one face, it has a plurality of mutually adjacently arranged detectors 30. In the illustrated exemplary embodiment, the detectors 30 have a resolution of 512×512 pixels with a pixel pitch of 0.1 mm. However, it is understood that it is also possible to utilize other resolutions. A center of the detector array 28 is denoted by D.

The workpiece 10 is arranged on a rotary table 40 during the measurement and preferably stands on a surface 42 of the rotary table 40. The rotary table 40 can rotate about a rotational axis 44, which preferably runs perpendicular to the surface 42. Rotating the rotary table 40 about the rotational axis 44 in the direction of an arrow 46 causes a rotation of the workpiece 10 about a corresponding rotational angle cp. In FIG. 3B, the reference signs of the elements moved by the rotation have been provided with an apostrophe.

Here it is understood that the spatially fixed arrangement of the radiation source 22 and the detector array 28, and also the rotatable arrangement of the workpiece 10, should likewise only be understood to be exemplary, and this does not restrict the present invention. On the one hand, in a kinematic reversal, the workpiece can also be fixed and the radiation source can rotate together with the detector array. Furthermore, the radiation source can be fixed and it is only the radiation that is deflected with changing direction. Finally, also another type of movement can be selected instead of a rotational movement.

The radiation source 30 and the center D of the detector array 28 are interconnected by a connection line 53, which defines a y-axis of a spatially fixed coordinate system x, y, z of the measuring station 20. The origin 47 of the spatially fixed coordinate system x, y, z is located within the rotary table 40 on the rotational axis 44. The z-axis coincides with the rotational axis 44. In the illustrated example, the origin 47 coincides with the center point M of the workpiece 10 for the purpose of clarity.

The detector array 28 is arranged relative to the spatially fixed coordinate system x, y, z such that the surface of said array runs in a plane parallel to the x-z plane and edges $29a$, $29c$ run parallel to the x-axis and the edges $29b$, $29d$ run parallel to the z-axis.

Figure 2B:
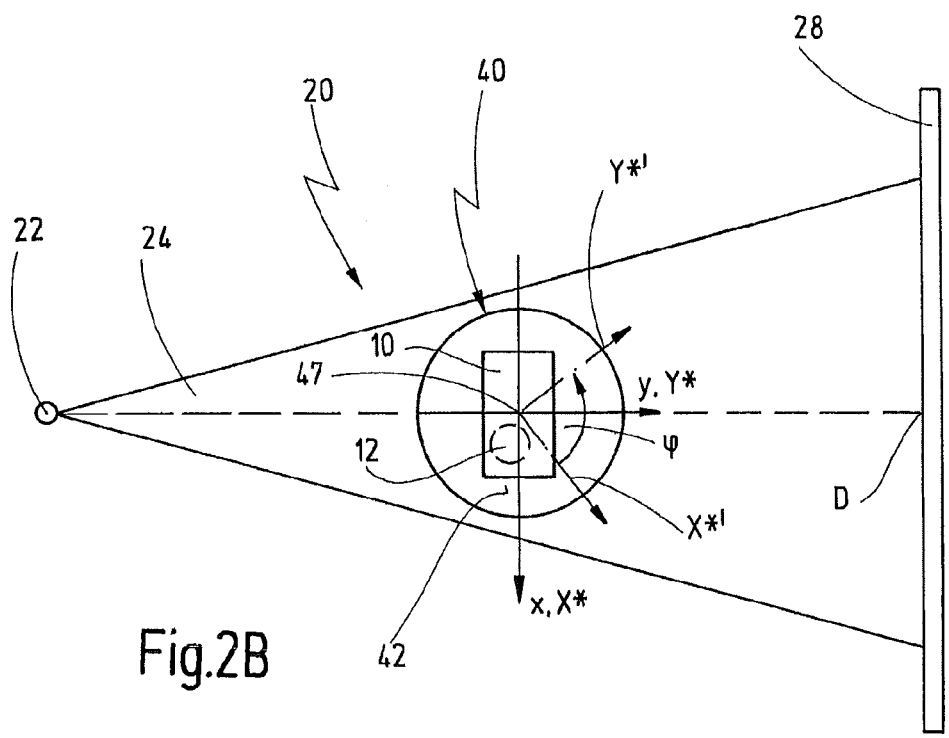
Figure 3A:
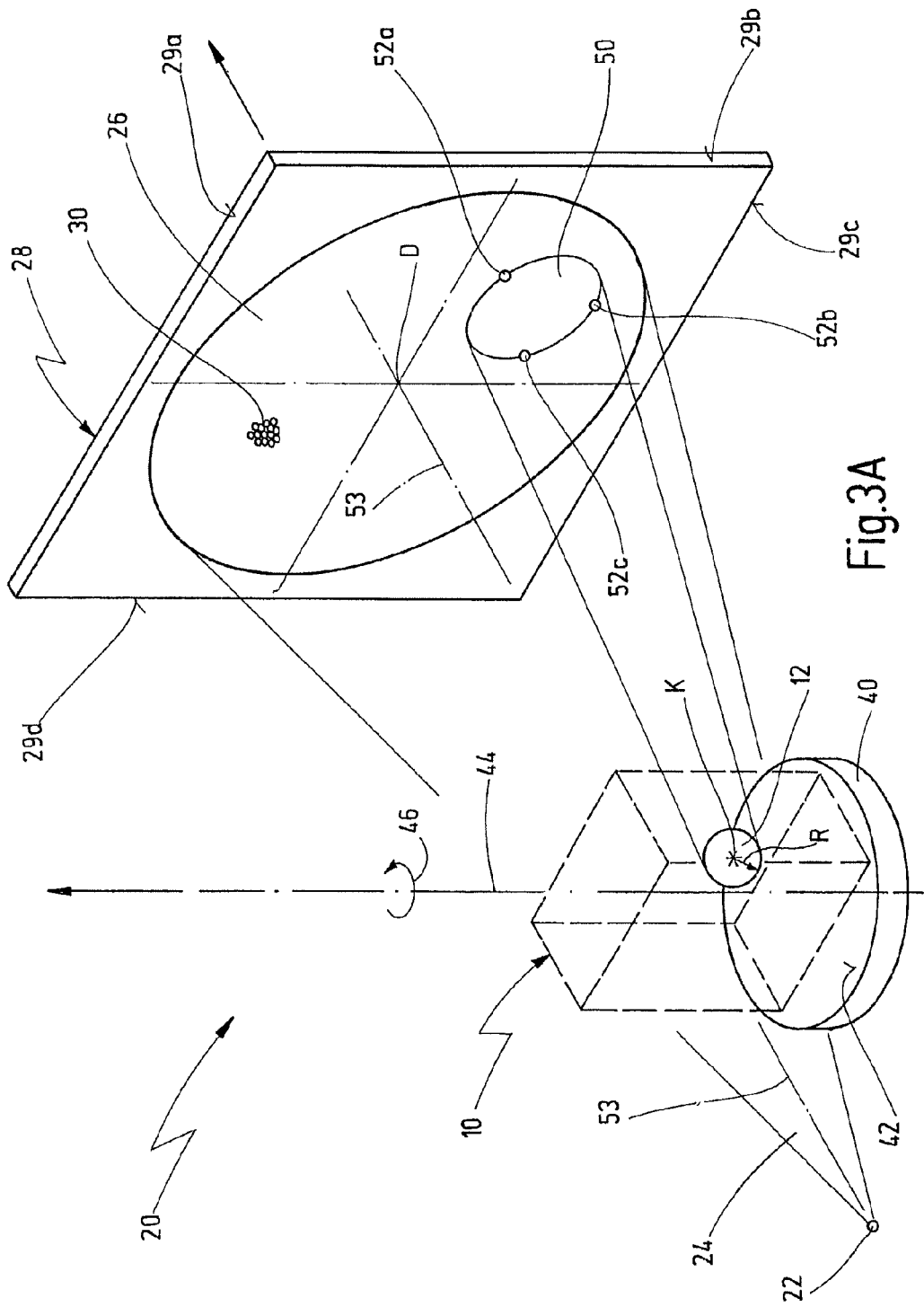

In the illustrated example, the center point M of the workpiece 10 on the rotary table 40 or the origin 47 of the spatially fixed coordinate system x, y, z is also the coordinate origin of a rotating coordinate system $x^*$, $y^*$, $z^*$, with the z and $z^*$ axes coinciding. The axes $x^*$ and $y^*$ rotate relative to the axes x and y, as illustrated in FIG. 2B by $x^{*\prime}$ and $y^{*\prime}$. The center point K of the spherical structure 12 is arranged at the position $x_k^*$, $y_k^*$, $z_k^*$ in the rotating coordinate system $x^*$, $y^*$, $z^*$, as shown in FIGS. 1A to 1C.

The irradiation of the workpiece 10 by means of the radiation source 22 results in a shadow of the spherical structure 12 in the workpiece 10 falling on the detector array 28, which shadow is in the form of a circular two-dimensional image 50 of the spherical structure 12. If the workpiece 10 is rotated about the rotational axis 44 ($z^*$-axis) by an angular step, the position of the image on the detector array 28 changes from 50 to 50', as illustrated in an exemplary fashion in FIG. 3B for a rotational angle $\phi=90°$.

As will be explained below, the position and the dimensions of the spherical structure 12, and hence a region of interest of the workpiece 10, are reconstructed from a plurality of images 50, 50', ... recorded at different angles φ by utilizing at least three measurement points 52a-52c, 52a'-52c' situated on a boundary of the images 50, 50'.

A first step determines the center point K, i.e. the position of the spherical structure 12 in respect of the spatially fixed coordinate system x, y, z, and the radius R of the structure 12. The measurement points 52a-52c, 52a'-52c' are registered for this purpose. In the process, the boundaries of the spherical projection, i.e. of the images 50, 50', are found by means of known methods for image processing or image analysis and are transformed into a suitable number of measurement points. For simplification purposes, three points are selected from these measurement points, which three points are preferably distributed approximately equidistantly over the circumference of the image.

In general terms, points are registered at high-contrast transitions in the images 50, 50', which transitions can correspond to image boundaries and edges of the structures to be examined In order to establish the position of the center point K and the radius R of the spherical structure 12, the coordinates $x_m$, and $z_m$ of the respective circle center $M_k$, $M_k'$ and the circle radius $R_k$, $R_k'$ of the images 50 and 50' are determined from the coordinates of the respective three measurement points 52a-52c, 52a'-52c' of the images 50, 50' utilizing the known equation of the circle illustrated in FIG. 3C:

$$(x-x_m)^2+(z-z_m)^2=R_k^2.$$

Now, center beams 54, 54' from the spot-like radiation source 22 to the center points $M_k$ and $M_k'$ of the images 50, 50' are established. The center beam 54' is then rotated back by the angular step φ by the radiation source 22 and the center point $M_k'$ being mathematically rotated back by −φ about the rotational axis 44 in order to compensate for the rotational movement of the rotary table 40.

In an ideal case, this would result in two center beams that coincide in space. However, despite very precise guides and control systems, there inevitably is a residual error in practice, and so the result of the calculation is not two coinciding straight lines, but two skewed straight lines. Now, points are determined on these two straight lines at which the distance between the straight lines is at a minimum. Then the connection perpendicular is constructed between these points. The center point of the path on the connection perpendicular between the two points is then assumed to be the best approximation for the location of the center point K in the x, y coordinate system.

Figure 4:
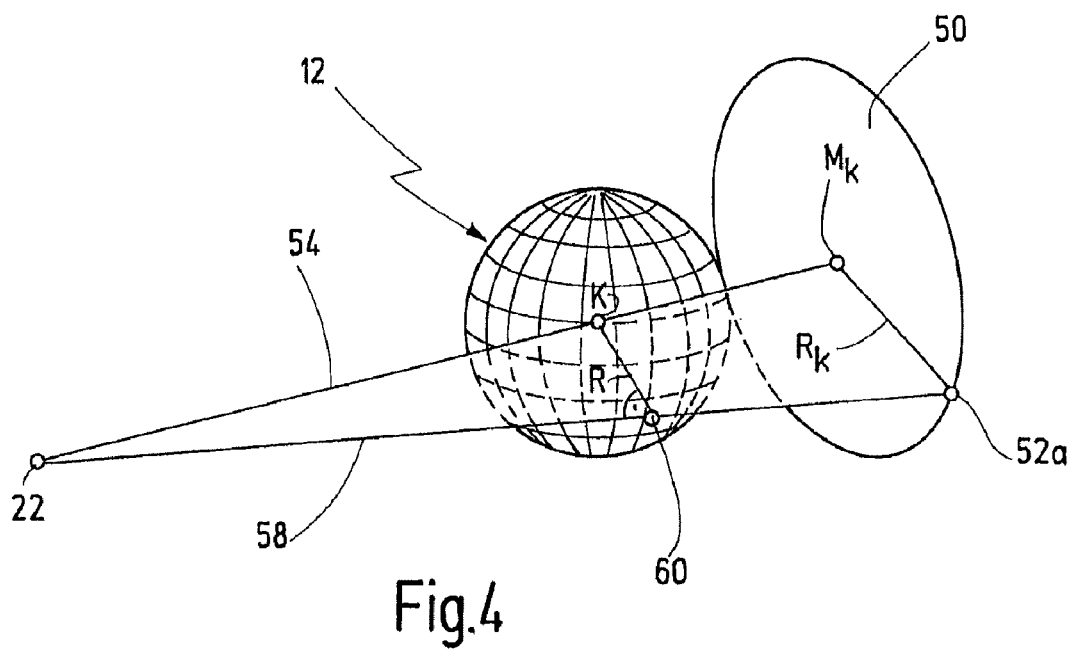
FIG. 4 shows an illustration to explain the determination of initial parameters.

Then, as illustrated in FIG. 4, the radius R of the structure 12 is determined by utilizing the intercept theorem. In the process, use is made of the fact that the ratio between the distance of the radiation source 22 from the center point $M_k$ of the image 50 and the distance of the radiation source 22 from the center point K of the structure 12 equals the ratio between the radius $R_k$ of the image 50 and the radius R of the structure 12.

Hence, initial values for a spherical equivalent body are set, namely the position of a center point $K_A$ and a radius $R_A$. Hence the equivalent body can already be determined approximately in respect of location and shape from these values, which result from only two measurements at different projections of the workpiece 10 on the detector array 28.

FIG. 4 furthermore shows that each tangent beam 58 leading from the radiation source 22 to a point 52 on the edge of the image 50 touches the structure 12 at a tangent point 60.

The path between the center point K and the tangent point 60, i.e. the radius R, is orthogonal on the tangent beam 58 in this case.

This tangent condition can be used to establish the associated tangent point 60 for each tangent beam 58 that grazes the structure 12 along a circumference. The tangent points 60 determined in this fashion can then be used for a best-fit calculation (e.g. a least-squares fit).

In the process, a set of improvements of the parameters of the equivalent body is calculated using a system of equations, preferably by calculating the derivatives in the determination equation of the tangent points at the locations of the individual tangent points together with the orthogonal distances between the tangent points and the equivalent body. In the process, use can be made of the known least-squares-fit method, but also of other methods (envelope fit, inscribed fit, Chebyshev fit). The tangent points are redetermined after each improvement in the parameters of the equivalent body. This optimization is carried out iteratively until the improvements fall below a predefined residual value. Hence, the optimum equivalent body is determined, and the residual distances of the tangent points to the equivalent body can be used for e.g. analyzing the shape deviations, as is conventional in 3D measuring technology. This method is known to a person skilled in the art.

As mentioned above, the characteristic data of the optimized equivalent body, that is to say the location of the center point K in the workpiece 10 and the radius R in the illustrated exemplary embodiment, are now compared to the data from the nominal structure predefined by construction. A good part/bad part decision is derived from this comparison, i.e. it is determined whether the workpiece 10 lies within predefined tolerances in respect of the structure.

Here the accuracy can be further increased by virtue of the fact that the tangent points 60 are determined in a plurality of projections or rotational positions φ of the workpiece 10, for example in 6 or 36 projections. The best-fit method is then applied to all tangent points 60 of the plurality of projections.

Figure 5:
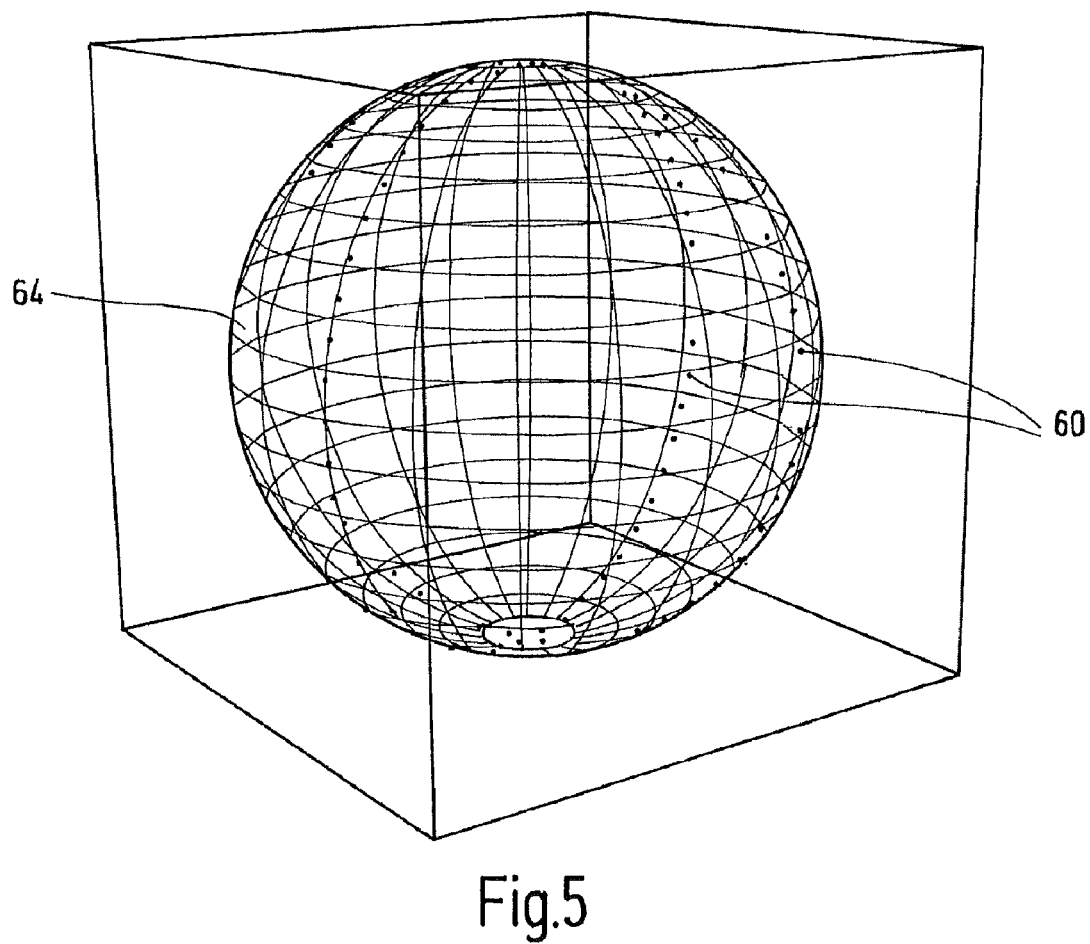
FIG. 5 shows an illustration of an equivalent body.

To this end, FIG. 5 shows an example of an optimized equivalent body 64 for a spherical structure, which was fitted into the tangent points 60 by six projections at different angles.

Instead of the approximation using the best-fit method, the equivalent bodies can also be determined using an envelope approximation, an inscribed approximation or a Chebyshev approximation.

The best-fit method described for a spherical equivalent body can also, as already mentioned, be used for a cylindrical or conical equivalent body if the structure 12 is cylindrical or conical. The initial parameters to be determined of the cylinder are the cylinder radius and the alignment of the cylinder axis. In the case of an equivalent cone, the initial parameters are the cone angle of the cone, the alignment of the cone axis and the position of the tip of the cone.

What is claimed is:

1. A method for measuring mechanical workpieces having a defined rotationally symmetric structure, the method comprising the steps of:
   providing a radiation source for generating radiation;
   providing a detector array for receiving the radiation, said detector array defining a two-dimensional imaging plane;
   positioning a workpiece between the radiation source and the detector array, so that the radiation penetrates the workpiece before it impinges on the detector array;
   moving the radiation source and the workpiece relative to one another in a step-by-step fashion;

generating a number of two-dimensional images of the workpiece by means of the detector array for a plurality of movement positions of the workpiece; and computing a three-dimensional image of the structure from the two-dimensional images, wherein the step of computing comprises:

detecting a high-contrast transition, which correspond to edges of the structure, in said two-dimensional images;

registering points at said high-contrast transition from at least two two-dimensional images generated at two different movement positions; and determining a three-dimensional geometric equivalent body using the registered points; and comparing said equivalent body to a predefined nominal structure;

wherein the geometric equivalent body only parameterizes said rotationally symmetric structure; and further wherein coordinates of a center point of the equivalent body are determined comprising the steps of:

a) determining first coordinates of at least three points on a boundary of a first circular image of the structure in a first movement position of the workpiece;

b) determining a first center point of the first circular image from the first coordinates;

c) rotating the workpiece on the one hand, and the radiation source and the detector array on the other hand relative to one another by a predefined angular step from the first into a second movement position;

d) determining second coordinates of at least three points on the boundary of a second circular image of the structure in the second movement position of the workpiece;

e) determining a second center point of the second circular image from the second coordinates;

f) determining a first center beam extending from the radiation source to the first center point and determining a second center beam extending from the radiation source to the second center point;

g) determining a position of the smallest distance between the first and second center beams; and h) determining coordinates of a center of the smallest distance as the position of the center point of the equivalent body.

2. The method of claim 1, wherein said step of detecting the high-contrast transition comprises extracting object boundaries of the structure from the two-dimensional images by means of an edge recognition.

3. The method of claim 1, wherein tangent points are determined, at which a tangent beam of the radiation leading from the radiation source to one of the points touches the structure, and wherein the tangent points are used for a best-fit calculation of the equivalent body.

4. The method of claim 1, wherein the equivalent body is determined without reconstructing a complete density distribution of the workpiece.

5. The method of claim 1, wherein the nominal structure is a rotationally symmetric structure.

6. The method of claim 5, wherein the nominal structure is at least one of a sphere, a cylinder, or a cone.

7. The method of claim 1, wherein the radiation source and the detector array are stationary in space and the workpiece is rotated about a rotational axis in predefined angular steps for the relative movement.

8. The method of claim 1, wherein a radius of the equivalent body is determined.

9. The method of claim 8, wherein determining the radius comprises the steps of:

i) determining a first distance between the radiation source and one of the first and second center points;

j) determining a second distance between the radiation source and the center point of the equivalent body; and k) determining a radius of one of said first and second circular images; and l) multiplying the radius of said one circular image by a ratio between the second and the first distance.

10. The method of claim 1, wherein the radiation source is a spot-like radiation source generating a cone of radiation.

11. The method of claim 1, wherein the radiation source is an x-ray radiation source.

12. A method for measuring mechanical workpieces having a rotationally symmetric structure, wherein a workpiece and radiation from a radiation source penetrating the workpiece are moved relative to one another step-by-step, wherein a two-dimensional image of the workpiece is generated in an imaging plane from the interaction of the workpiece and the radiation in each movement position of the workpiece, and wherein a three-dimensional image of the structure is computed from the two-dimensional images, wherein, from at least two two-dimensional images of the workpiece generated at two different movement positions, points which correspond to edges of the structure are registered at a high-contrast transition in said two-dimensional images, wherein a three-dimensional geometric equivalent body is determined from the position of the registered points, wherein said equivalent body is compared to a predefined nominal structure, and wherein the geometric equivalent body only parameterizes individual rotationally symmetric elements of the workpiece, which are imaged in the two-dimensional images with clear-cut, high-contrast object boundaries, and further wherein the rotationally symmetric structure is a spherical structure, and wherein coordinates of a center point of the equivalent body are determined by the following steps taken in order:

a) determining first coordinates of at least three points on the boundary of a first circular, two-dimensional image of the structure in a first movement position of the workpiece;

b) determining a first center point of the first circular image from the first coordinates;

c) rotating the workpiece on the one hand, and the radiation source and the imaging plane on the other hand relative to one another by a predefined angular step into a second movement position of the workpiece;

d) determining second coordinates of at least three points on the boundary of a second circular, two-dimensional image of the structure in the second movement position of the workpiece;

e) determining a second center point of the second circular image from the second coordinates;

f) determining two center beams between the radiation source and the first and second center points, respectively;

g) determining a position of a smallest distance between the center beams;

h) dropping a perpendicular between the center beams at the position of the smallest distance; and i) determining coordinates of a midpoint of the perpendicular as the position of the center point of the equivalent body.

13. The method of claim 12, wherein the radiation source and the imaging plane for the relative movement are fixed in space and the workpiece is rotated about a rotational axis in predefined angular steps.

14. The method of claim 12, wherein a radius of the equivalent body is determined by the following steps taken in order:
j) determining a first distance between the radiation source and the center point of the circular image;
k) determining a second distance between the radiation source and the center point (K) of the actual structure; and
l) multiplying the radius of the circular image by the ratio between the second and the first distance.

15. The method of claim 14, wherein tangent points are determined for the at least three points established in step a), at which tangent points a beam between the radiation source and said at least three points touches a boundary of the structure generating the first circular image, and wherein the equivalent body is fitted into a point cloud formed by the points, wherein the center point and the radius determined in steps i) and l) are used as initial values.

16. The method of claim 15, wherein the point cloud is formed from tangent points established in different rotational positions of the workpiece.

* * * * *